United States Patent [19]
Fleischhacker et al.

[11] Patent Number: 5,676,662
[45] Date of Patent: Oct. 14, 1997

[54] ABLATION CATHETER

[75] Inventors: John J. Fleischhacker, Minnetonka, Minn.; John F. Swartz, Tulsa, Okla.

[73] Assignee: Daig Corporation, Minnetonka, Minn.

[21] Appl. No.: 407,448

[22] Filed: Mar. 17, 1995

[51] Int. Cl.⁶ ..................................... A61B 17/39
[52] U.S. Cl. .................. 606/41; 606/45; 607/115; 607/122; 128/642
[58] Field of Search .............. 606/37–42, 45–52, 606/29–31; 607/115, 116, 122, 100–102; 128/642

[56] References Cited

U.S. PATENT DOCUMENTS

| | | |
|---|---|---|
| 3,572,344 | 3/1971 | Bolduc . |
| 4,161,952 | 7/1979 | Kinney et al. . |
| 4,481,953 | 11/1984 | Gold et al. . |
| 4,641,649 | 2/1987 | Walinsky et al. . |
| 4,776,334 | 10/1988 | Prionas . |
| 4,860,769 | 8/1989 | Fogarty et al. . |
| 4,934,049 | 6/1990 | Kiekhafer et al. . |
| 5,115,818 | 5/1992 | Holleman et al. . |
| 5,334,193 | 8/1994 | Nardella . |
| 5,336,253 | 8/1994 | Gordon et al. . |
| 5,354,297 | 10/1994 | Avitall . |

FOREIGN PATENT DOCUMENTS

| | | |
|---|---|---|
| 0392837 | 10/1990 | European Pat. Off. . |
| WOA9510319 | 4/1995 | WIPO . |

OTHER PUBLICATIONS

Saul, P.S. et al. "Catheter Ablation of Accessory Atrioventricular Pathways in Young Patients: Use of Long Vascular Sheaths, the Transseptal Approach and a Retrograde Left Posterior Parallel Approach," J. Amer. Coll. Card., vol. 21, No. 3, pp. 571–583 (1993).

Swartz J.F. et al. "Radiofrequency Endocardial Catheter Ablation of Accessory Pathway Atrial Insertion Site, Circulation", vol. 87, No. 2, pp. 487–499 (1993).

*Primary Examiner*—Lee S. Cohen
*Assistant Examiner*—Michael Peffley
*Attorney, Agent, or Firm*—Scott R. Cox

[57] ABSTRACT

A catheter for mapping and ablating cardiac tissue comprising an elongated catheter body with proximal and distal ends and an electrode comprising an electrode conductor and a helical electrode comprising a series of turns which is secured to the catheter body near its distal end, wherein at least a portion of the circumference of the turns of the helical electrode portion is uncoated. Also disclosed is a process for ablating human tissue wherein a helical electrode secured to a catheter body near its distal end is utilized for an ablating procedure.

4 Claims, 4 Drawing Sheets

ABLATION CATHETER

BACKGROUND OF INVENTION

1. Field of Invention

This invention relates to catheters for the mapping and ablation of biological tissue, particularly cardiac tissue. In particular, it relates to an electrode catheter with a helical electrode section secured to the outside surface of a catheter body used for the mapping and ablating of cardiac tissue.

2. Prior Art

Catheters have been in use for medical procedures for many years. For example, one use of electrode catheters has been to convey an electrical stimulus to a selected location within the human body. Another use for sensing electrode catheters has been the monitoring of various forms of activity by diagnostic tests within the human body. Catheters can be used to examine, diagnose and treat while positioned at a specific location within the body which is otherwise inaccessible without more invasive procedures. Catheters may be inserted into veins or arteries near the body surface. These catheters are then guided to a specific location for examination, diagnosis or treatment by manipulating the catheter through the artery or vein of the human body.

Catheters, such as electrode catheters, are used increasingly for medical procedures involving the human heart. In these procedures a catheter is typically advanced to the heart through veins or arteries and then is positioned at a specified location within the heart. Typically, the catheter is inserted in an artery or vein in the leg, neck or arm of the patient and threaded, sometimes with the aid of a guidewire or introducer, through the various arteries or veins until the distal tip of the catheter reaches the desired location in the heart.

An increasingly utilized procedure for the treatment of certain types of cardiac arrhythmia is catheter ablation. Catheter ablation uses an energy source to create a permanent scar to interrupt or modify existing conduction pathways associated with arrhythmias within the heart. The particular area for ablation depends on the type of underlying arrhythmia. One common ablation procedure is for the treatment of atrioventricular nodal reentrant tachycardia (AVNRT). Ablation of the fast or slow AV nodal pathways has become an accepted treatment for AVNRT. See Singer, I., et al., "Catheter Ablation for Arrhythmias" *Clinical Manual of Electrophysiology*, pp. 421–431 (1993); Falk, R. H., et al., *Atrial Fibrillation Mechanisms in Management*, pp. 359–374 (1992); Horowitz, L. N., *Current Management of Arrhythmias*, pp. 373–378 (1991); and Martin, D., et al., *Atrial Fibrillation*, pp. 42–59 (1994). The use of electrode catheters for ablating locations within the heart has also been disclosed, for example in U.S. Pat. Nos. 4,641,649, 5,263,493, 5,231,995, 5,228,442 and 5,281,217.

Catheter ablation of accessory pathways associated with Wolff-Parkinson-White syndrome using a long vascular sheath using both a transseptal and retrograde approach is discussed in Saul, J. P., et al. "Catheter Ablation of Accessory Atrioventricular Pathways in Young Patients: Use of long vascular sheaths, the transseptal approach and a retrograde left posterior parallel approach" *Journal of the American College of Cardiology*, Vol. 21, no. 3, pps. 571–583 (Mar. 1, 1993). See also Swartz, J. F. "Radiofrequency Endocardial Catheter Ablation of Accessory Atrioventricular Pathway Atrial Insertion Sites" *Circulation*, Vol. 87, no. 2, pps. 487–499 (Feb. 1993).

Ablation procedures for treatment of atrial fibrillation in the left and right atrium have also been disclosed in copending applications, Ser. Nos. 08/272,014 and 08/337,722. For this procedure, lines of ablation or linear ablation tracks must be produced as an element of the ablation procedures in the left and right atrium. Surgical procedures for the treatment of atrial fibrillation which also produce scars in the heart have been reported in Cox, J. L. et al. "The Surgical Treatment of Atrial Fibrillation," *Journal of Thoracic and Cardiovascular Surgery*, Vol. 101, No. 4, pages 569–83 (1989). In this procedure, appropriately placed incisions are made through the atria which produces scars which interrupt the pathways of the most common reentrant circuits.

The sources of energy used for catheter ablation vary. Initially, high voltage, direct current (DC) ablation techniques were commonly used. However, because of problems associated with the use of DC current, radio frequency (RF) has become the preferred source of energy for ablation procedures. The use of RF energy for ablation has been disclosed, for example, in U.S. Pat. Nos. 4,945,912, 5,209,229, 5,281,218, 5,242,441, 5,246,438, 5,281,213 and 5,293,868.

In addition, the use of radio frequency energy by an ablation catheter for the treatment of Wolff-Parkinson-White syndrome in the left atrium by use of a transseptal sheath is disclosed in Swartz, J. F. et al. "Radiofrequency Endocardial Catheter Ablation of Accessory Atrioventricular Pathway Atrial Insertion Sites" *Circulation* 87:487–499 (1993). See also Tracey, C. N. "Radio Frequency Catheter Ablation of Ectopic Atrial Tachycardia Using Paced Activation Sequence Mapping" *J. Am. Coll. Cardiol.* 21:910–917 (1993).

Ablation of a precise location within the heart requires the precise placement of the ablation catheter within the heart. Precise positioning of the ablation catheter is especially difficult because of the physiology of the heart, particularly as the ablation procedures generally occur while the heart is beating. Commonly, the choice of placement of the catheter is determined by a combination of electrophysiological guidance and fluoroscopy (placement of the catheter in relation to known features of the heart which are marked by radiopaque diagnostic catheters which are placed in or at known anatomical structures, such as the coronary sinus, high right atrium and the right ventricle).

Many early ablation procedures were conducted with a separate ablation catheter utilizing a single distal electrode tip for the ablation procedures. Increasingly, however, cardiac mapping requires that multiple electrodes be affixed to the catheter so that mapping and ablation could be conducted with the same catheter.

The use of multiple electrodes on a conventional catheter body has also been used to alternately map or ablate at a number of different locations in the heart using the same catheter. These catheters conventionally contain a distal tip electrode and a plurality of ring electrodes circling the catheter at various distances from the tip electrode. See, for example, U.S. Pat. Nos. 4,892,102, 5,025,786, 5,327,905, and 5,354,297.

An ablation catheter for use in the heart which contains a pair of intertwined helical electrodes is disclosed in U.S. Pat. No. 5,334,193. The helically oriented electrode is affixed to the surface of the catheter body over a distance of about 8 cm. at the distal end of the catheter body.

Other helical electrodes for defibrillation are disclosed in U.S. Pat. Nos. 4,934,049, 4,860,769 and 4,161,952. See also U.S. Pat. Nos. 3,572,344 and 4,481,953.

During a conventional ablation procedure the energy, such as RF energy, is delivered to the cardiac tissue through the tip electrode. As a result of the use of this energy, there is an associated temperature rise on the surface of the ablated tissue. This rise in tissue temperature in turn causes a rise in the temperature of the tip electrode which can result in coagulation of adjacent body fluids, particularly blood, which reduces the effectiveness of the ablation procedure.

To achieve efficient and effective ablation, it is important to avoid the coagulation problems that are associated with high energy delivery to conventional ablation catheters. This coagulation problem can be significant when linear ablation tracks are produced during an ablation procedure. Notwithstanding it is critical for effective ablation that the linear ablation tracks be carefully monitored to assure that a completely ablated scar has been produced.

It is accordingly an object of this invention to disclose a catheter for mapping and ablating tissue within the human heart.

It is a still further object of this invention to disclose a catheter containing a helical electrode near the distal end of a catheter body for creating a linear ablation track within the human heart during an ablation procedure.

It is a still further object of this invention to disclose a catheter with a helical electrode near the distal end of the catheter wherein only a portion of the surface of the helical section of the electrode is exposed.

It is a still further object of this invention to disclose a catheter for the ablation of cardiac tissue containing a helical electrode, wherein a portion of the body of the catheter extends between the individual coils of the helical electrode.

It is a still further object of this invention to disclose a catheter with a helical electrode for use in the ablation of a line of tissue within the heart wherein the temperature during the ablation procedure is monitored at more than one point on the helical electrode.

It is a still further object of this invention to disclose a helical electrode catheter for use in the ablation of a track of tissue within the heart wherein the helical electrode is comprised of two or more separate portions which can be joined together to form a single electrode for ablation or be separated for use in mapping procedures.

It is a still further object of this invention to disclose a method for the ablation of cardiac tissue by use of an ablation catheter containing a helical electrode near the distal end of the catheter body for creating a linear ablation track within the heart during an ablation procedure.

These and other objects can be obtained by the disclosed catheter for the mapping and ablation of cardiac tissue which is disclosed by the instant invention.

SUMMARY OF INVENTION

The instant invention is a catheter for the mapping and ablating of human tissue comprising (a) a catheter body with proximal and distal ends containing one or more lumen running therethrough from the proximal to the distal ends and (b) an electrode, comprising one or more electrode conductors and a helical electrode portion containing individual turns, wherein the individual turns are separated by a linear distance, wherein the electrode conductor or conductors pass through the lumen of the catheter body to be secured with the helical electrode portion, wherein the helical electrode portion is secured to the catheter body near its distal end, wherein a portion of the catheter body extends between individual turns of the helical electrode portion, and wherein a portion of the surface of the individual turns of the helical electrode portion is uncoated.

In a preferred embodiment the helical electrode portion of the catheter is uncoated in a longitudinal line of the helical electrode portion, wherein only this longitudinal line of the coiled electrode section is utilized for ablation or mapping.

In another preferred embodiment there is disclosed a process for the ablation of human tissue comprising (a) introducing into the human body a guiding introducer or guiding introducer system containing a proximal and distal end with at least one lumen running therethrough, (b) directing the guiding introducer to the human tissue in the human body to be ablated, (c) introducing into the lumen of the guiding introducer an ablation catheter comprising an elongated catheter body with proximal and distal ends containing one or more lumen running therethrough and an electrode, wherein said electrode comprises an electrode conductor or conductors passing through the lumen of the catheter body and a helical electrode portion containing individual turns, wherein the individual turns are separated by a linear distance, wherein said coiled electrode portion is secured to the catheter body and wherein a portion of the surface of the individual turns of the helical electrode section is uncoated and (d) ablating the human tissue using the ablation catheter.

DETAILED DESCRIPTION OF THE PREFERRED EMBODIMENT

Figure 1:
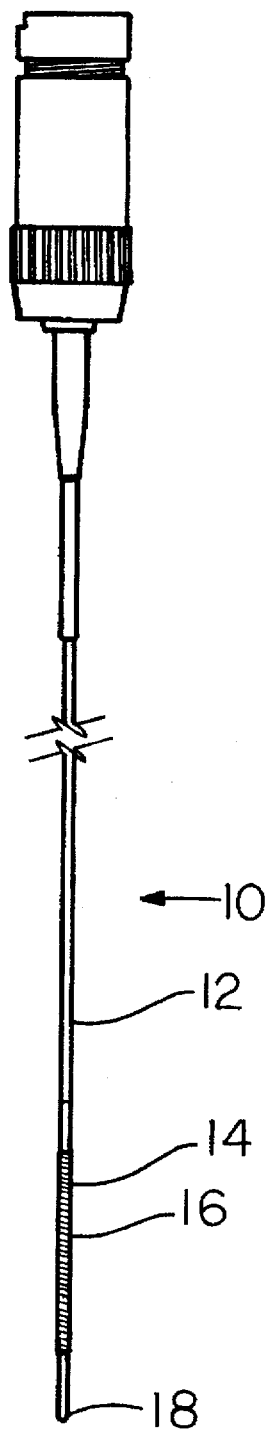
FIG. 1 is a side view of the ablation catheter.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle.

In the normal heart, contraction and relaxation of the heart muscle (myocardium) takes place in an organized fashion as electro-chemical signals pass sequentially through the myocardium from the sinoatrial (SA) node to the atrialventricular (AV) node and then along a well defined route which includes the His-Purkinje system into the left and right ventricles. Initial electrical impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus by-passing the normal His-Purkinje system. These pathways are usually located in the fibrous tissue that connects the atrium and the ventricle.

Other abnormal arrhythmias sometimes occur in the atrium, which are referred to as atrial arrhythmia. Three of the most common atrial arrhythmia are ectopic atrial tachycardia, atrial fibrillation and atrial flutter. Atrial fibrillation can result in significant patient discomfort and even death because of a number of associated problems, including: (1) an irregular heart rate which causes the patient discomfort and anxiety, (2) loss of synchronous atrioventricular contractions which compromises cardiac hemodynamics resulting in varying levels of congestive heart failure, and (3) stasis of blood flow, which increases the likelihood of thromboembolism. It is sometimes difficult to isolate a specific pathological cause for atrial fibrillation although it is believed that the principle mechanism is one or a multitude of reentry circuits within the left and/or right atrium. Efforts to alleviate these problems in the past have included significant usage of pharmacological treatments. While pharmacological treatments are sometimes effective, in most or certain circumstances drug therapy is of limited effectiveness and frequently it is plagued with side effects such as dizziness, nausea, vision problems and other difficulties.

It has been discovered that atrial arrhythmias can be treated by the use of ablation procedures performed within the left and right atrium of the heart. However, to accomplish this result, one must ablate predetermined locations within the atria to form linear tracks or scars through the walls (transmural) of the atria of the heart, thus forming a natural barrier to the formation of reentry circuits. These transmural scars are similar in function to the scars formed by the surgical procedures proposed by Dr. Cox, for example in Cox, J. L. et al., "The Surgical Treatment of Atrial Fibrillation," *J. Thoracic Cardiovasc. Surgery*, 101:402–426 (1991). To be effective, these linear scars must be in well defined locations in the heart. In addition, it is critical for proper lesion formation that adequate contact pressure be maintained between the ablation catheter electrode and the heart tissue to be ablated to achieve a consistent linear scar with adequate depth in the heart tissue.

The ablation catheters used to perform the ablation procedures produce scar tissue at a selected site. The energy necessary to ablate the tissue and create a permanent scar can be provided by a number of different sources. Originally direct current was utilized to provide the energy for ablation procedures. Laser, microwave, ultrasound and other forms of direct current (high energy, low energy and fulgutronization procedures) have also been utilized to perform ablation procedures. However, the preferred source of energy for the ablation procedures of the instant invention is RF energy.

One of the significant difficulties in performing any cardiac procedure in the heart is caused by the physiology of the heart when beating, especially if that beating is abnormal. The preferred procedure for the creation of ablation tracks within the heart requires the precise positioning and contact pressure of the ablation electrode or electrodes of the ablation catheter against the heart tissue to ablate a predetermined track in the tissue of the heart.

In the past, ablation procedures performed using catheters have conventionally utilized only the distal tip electrode. While ablation using only a tip electrode can be successful in ablating a specific point in the heart, ablation procedures utilizing only a tip electrode to form linear tracks within the heart are difficult. To ablate linear tracks within the heart using a conventional ablation tip electrode, procedures such as a "drag burn" have been utilized. During this procedure, while RF energy is being applied, the catheter tip electrode is drawn across the tissue to be ablated, producing a line of ablation at a predetermined location within the heart. Alternatively, a line of points of ablation can be created by moving the ablation catheter incremental distances across the cardiac tissue to achieve the linear ablation track. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of the ablation procedure and other variables associated with the nature of a beating heart, especially an erratically beating heart. Unless an uninterrupted track of cardiac tissue is ablated, holes in the linear scar can remain, permitting the continuation of the reentry circuit which causes the arrhythmia.

It has been discovered that more efficient ablation may be achieved if a linear track of cardiac tissue is ablated at the same time. Conventional tip electrodes with adjacent ring electrodes cannot perform this procedure because of the high amount of energy that is necessary to ablate sufficient tissue to achieve an adequate linear scar. Also, conventional ring electrodes when used to ablate cardiac tissue may leave holes or gaps in the ablation scar, which can provide a doorway through the scar for the creation of a new reentry circuit.

The device of the instant invention is designed to produce a complete linear ablation track which avoids the problems of earlier ablation devices. In addition, the process disclosed herein discloses an efficient procedure for the creation of the linear scars or ablation tracks.

The ablation catheter (10) is comprised of two main elements, the catheter body (12) and the electrode (14). See FIG. 1. The catheter body is a conventional elongated catheter made of materials suitable for use in humans, such as nonconductive polymers. The materials should not be thermally insulating and should facilitate effective heat transfer. Exemplary polymers used for the production of the catheter body include those well known in the art such as polyolefins, nylons, polytetrafluoroethylene, polyvinylidene fluoride, and fluorinated ethylene-propylene polymers.

The diameter of the catheter is within ranges well known in the industry. Preferably, the diameter of the catheter body is within the range of about 2 to 14 French (1 French equals ⅓ of a millimeter). The catheter body preferably contains one or more lumen running therethrough from the proximal end to near or at the distal end of the catheter. There should be sufficient lumen to permit the wires of the electrode conductor or conductors to pass therethrough.

Figure 2:
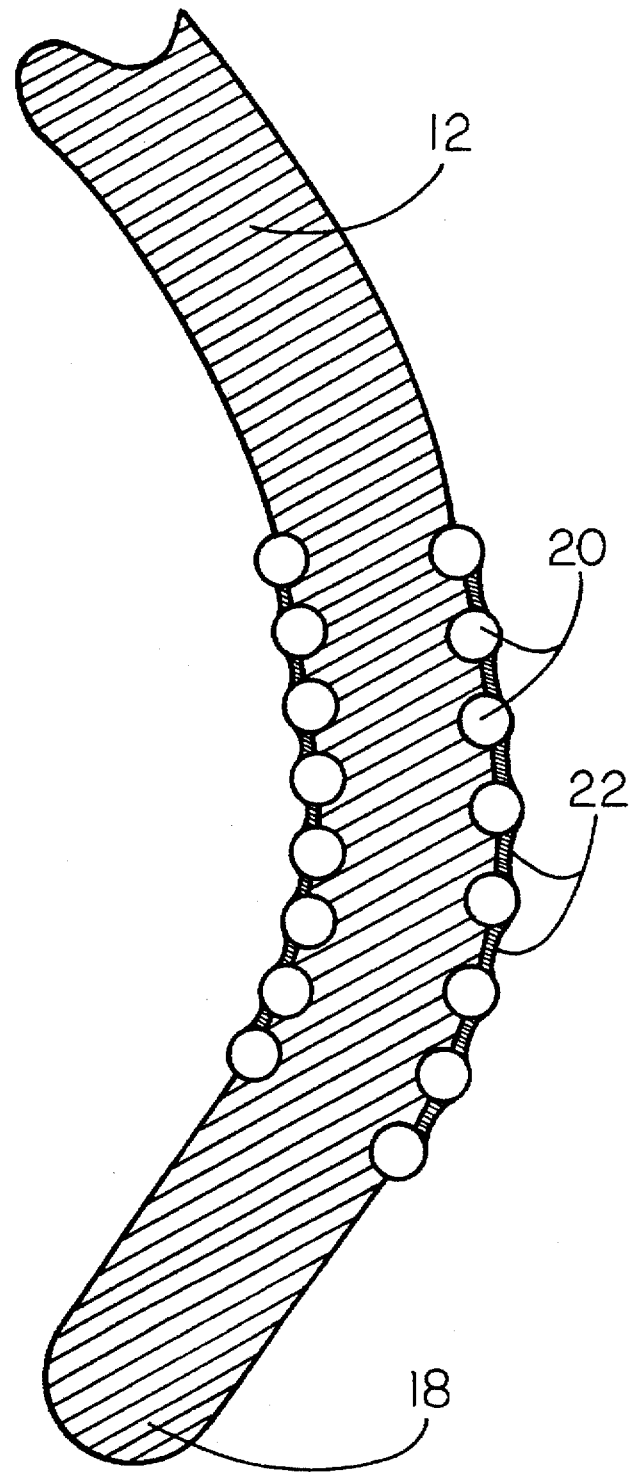
FIG. 2 is a side view of the distal end of the catheter showing one preferred embodiment of the helical electrode portion, wherein the individual turns of the helical electrode portion are partially coated.
Figure 3:
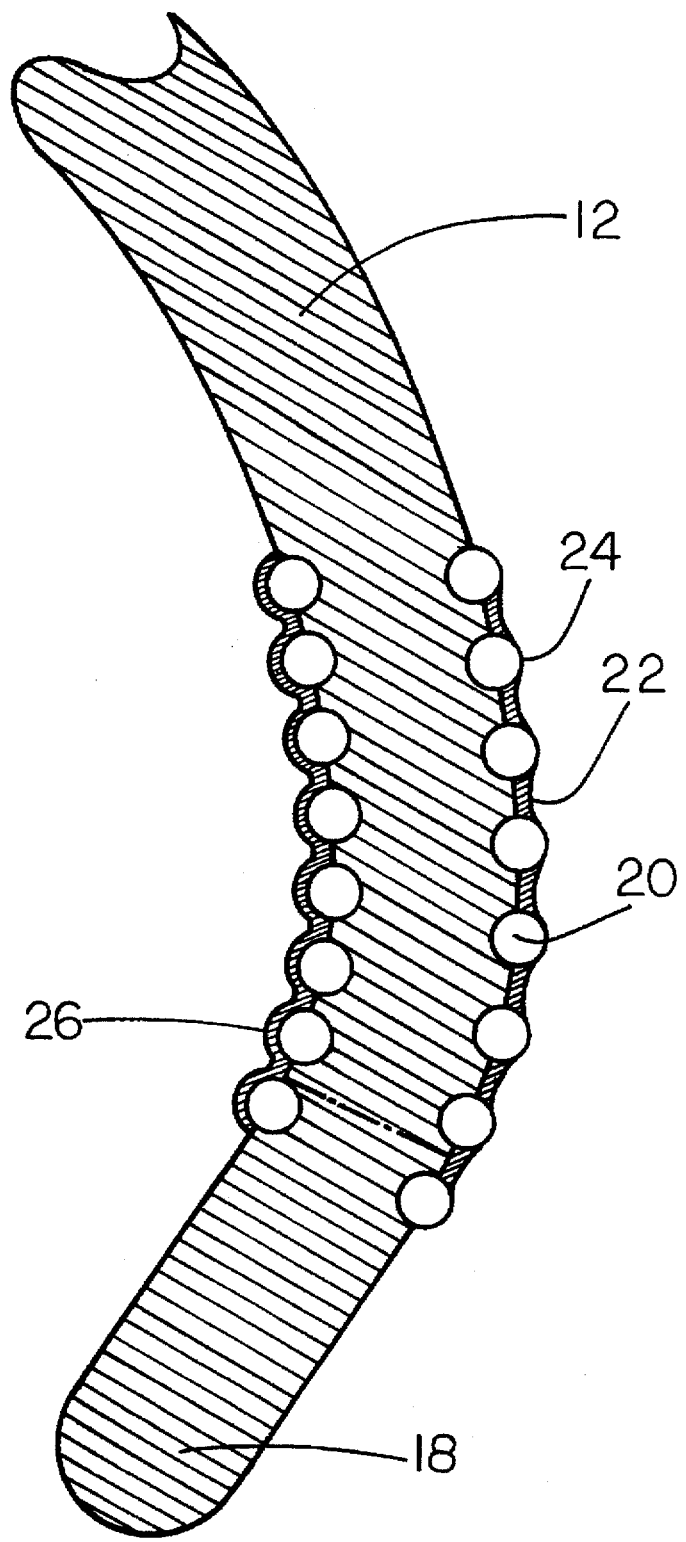
FIG. 3 is a cutaway side view of the distal end of the catheter showing a second preferred embodiment of the helical electrode portion, wherein a portion of the circumference of the helical electrode is entirely coated and a portion uncoated.

The electrode conductor or conductors, which pass from the proximal end of the catheter through the lumen of the catheter body, exit the catheter through an exit port or ports in the surface of the catheter body, preferably within about 1 to about 5 cm. from the distal end of the catheter. The electrode conductor then forms a helical electrode portion (16) around the outside surface of the catheter body ending preferably at least about 1.0 to 0.5 cm. from the distal tip of the catheter. See FIGS. 2 and 3. It is preferable that the helical electrode portion (16) not extend to the distal tip (18) of the catheter so that the tip portion of the catheter body can be used as an anchor or support during an ablation procedure.

Figure 4:
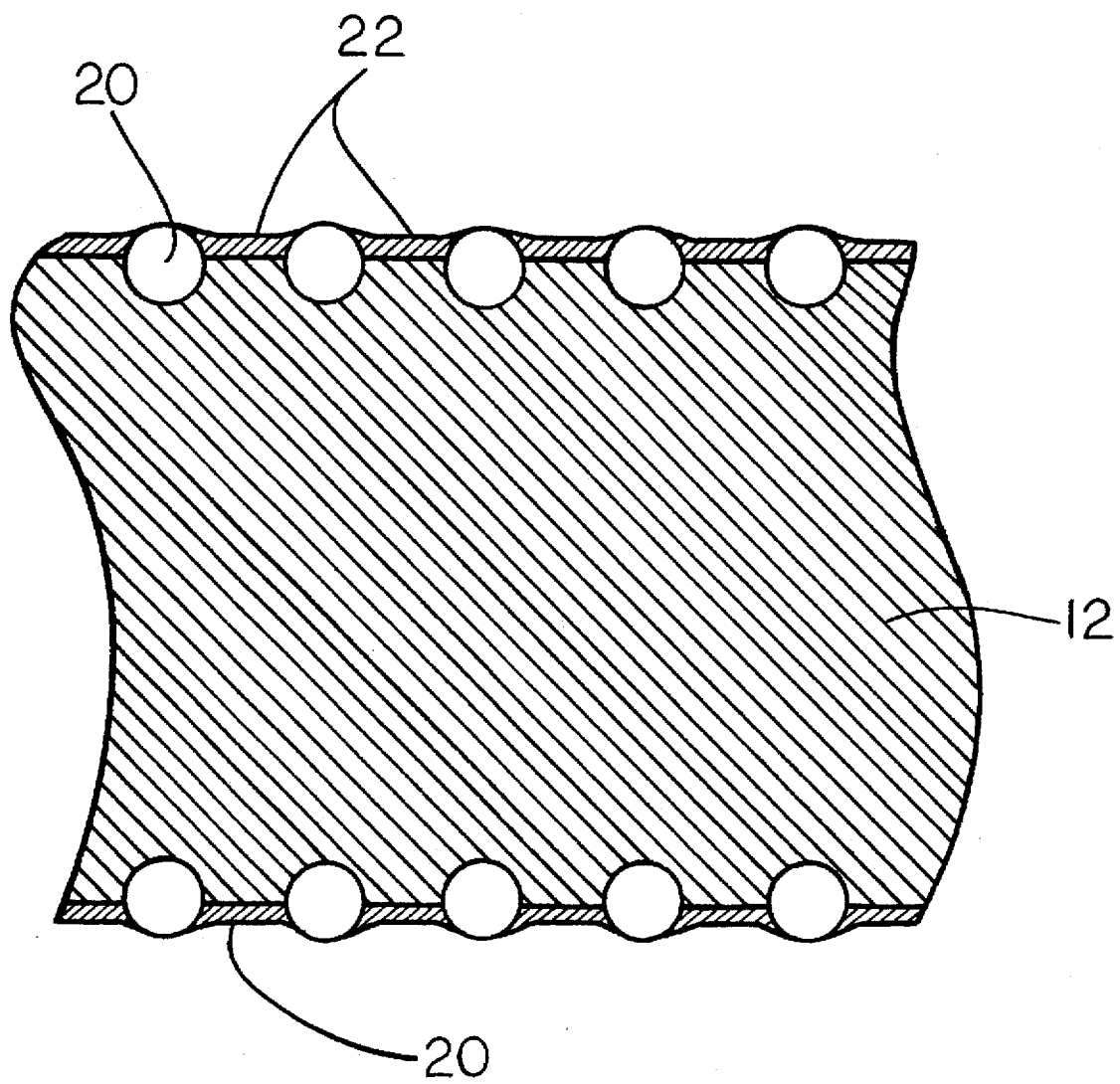
FIG. 4 is a cutaway view of the helical electrode portion.

The helical electrode portion (16) contains a number of individual turns (20) spaced sufficiently close to each other to provide sufficient overlap during an ablation procedure from turn to turn to produce a uniform linear ablation track. See FIG. 4. The linear distance between the individual turns is preferably about 0.1 to about 4.0 mm. and most preferably between about 0.3 and 1.0 mm. It is critical that a consistent linear distance between the individual turns of the helical electrode portions be maintained. Without this consistency, ablation procedures may not produce an adequate ablation scar with sufficient depth, cross-section and continuity.

The helical electrode portion (16) is formed from conventional electrode materials such as platinum and is preferably from about 0.007 in. to about 0.015 in. in diameter. The length of the helical electrode portion in place on the ablation catheter (10) is from about 1.0 to about 8.0 cm. in length and preferably from about 1.0 to about 4.0 cm. Thus, preferably 8 to about 80 individual turns comprise the helical electrode portion and more preferably 10 to about 40 individual turns. (The number of turns shown in the Figures is for illustrative purposes only.)

Figure 5:
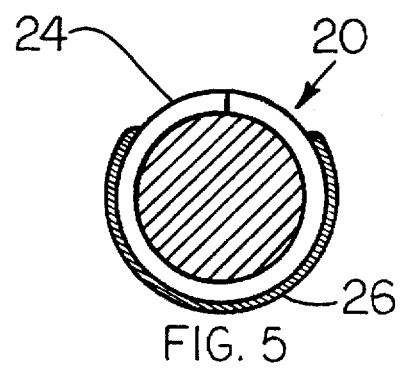
FIG. 5 is a cross-sectioned view of one turn of the helical electrode portion which is partially coated.

While the space (22) between the individual turns of the helical electrode portion need not be filled, preferably the space is partially filled. See FIGS. 2, 3 and 4. Preferably this filling of the space between the individual turns results in no more than about 10–50 percent of the circumference of each individual turn of the coiled electrode portion being uncoated by the filling material. See FIG. 5. Preferably the material used to fill the space (22) between the turns (20) is comprised of a conventional material, such as an urethane. By filling this space between the turns, the amount of potential coagulum buildup produced during the ablation procedure is significantly reduced. This limited exposure of the outside surface of the turns of the helical electrode portion also limits the amount of energy that is necessary for the ablation procedure. However, a portion of the outside surface of the turns of the helical electrode section must remain uncoated, preferably in a longitudinal line, to allow contact of the helical electrode section with the cardiac tissue to form the linear scar during the ablation procedure. See FIG. 3.

There are several methods of achieving the limited coating of the helical electrode portion (16). For example, the helical electrode portion may be completely coated with a conventional coating prior to securing it to the catheter body. After the helical electrode portion is secured to the catheter body (12), the coating material can be partially removed from the surface of the helical electrode portion by use of an abrasive means, leaving about 10 to about 50 percent of the circumference of the turns of the helical electrode portion uncoated. See FIG. 5. The remaining surface of the turns of the helical electrode portion is coated and/or isolated from the cardiac tissue and any surrounding blood.

Alternatively, the helical electrode portion (16) can be wound onto the catheter body (12) prior to coating. After such winding, the distal portion of the catheter body, including the helical coiled portion (16) can be dipped or sprayed, preferably with a urethane coating. This procedure backfills the space (22) between the individual turns of the helical coiled section. The coating material can then be partially removed by use of an abrasive, leaving about 10 to about 50 percent of the circumference of the turns of the helical electrode portion uncoated.

To further restrict the amount of cardiac tissue that is ablated during a single procedure by the ablation catheter (10), a portion of the coating on the helical electrode portion (16) can be removed only along one longitudinal linear section of the helical electrode portion. See FIG. 3. During operation, the uncoated linear section (24) of the helical electrode portion (16) is placed against the cardiac tissue to produce the ablation scar, while the coated portion (26) of the turns of the helical electrode portion opposite where the ablation procedure occurs will not radiate energy and thus will not heat the blood adjacent thereto. This also reduces the likelihood of production of coagulum. Only the uncoated section (24) of the helical electrode portion which is actually in intimate contact with the cardiac tissue will be uncoated and utilized for production of the ablation scar. This reduces the amount of coagulum formed and permits a more efficient cardiac ablation.

In an alternative preferred procedure to produce a helical electrode portion which is partially uncoated, at least about 40 percent of the circumference of an individual turn of the helical electrode portion is secured within a groove which is preformed in a portion of the outside surface of the catheter body near its distal end. By this procedure no filling of the space between the individual turns of the helical electrode portion is necessary. Of course, if desired, additional fill can be added between the individual coils thus leaving only a portion of the circumference of the individual turns of the helical electrode portion uncoated, preferably in a longitudinal, linear line. See FIG. 3. Preferably at least about 10 percent of the circumference of the individual turns remains uncoated for efficient ablation procedures. The grooves in the catheter body are formed using procedures known in the industry to produce such grooves. Preferably the grooves should be deep enough to cover at least about half of the circumference of the turns. Greater or lesser percentages of the surface can be covered as long as an adequate linear portion of the individual turns remain uncoated and thus available for use for ablation.

Figure 6:
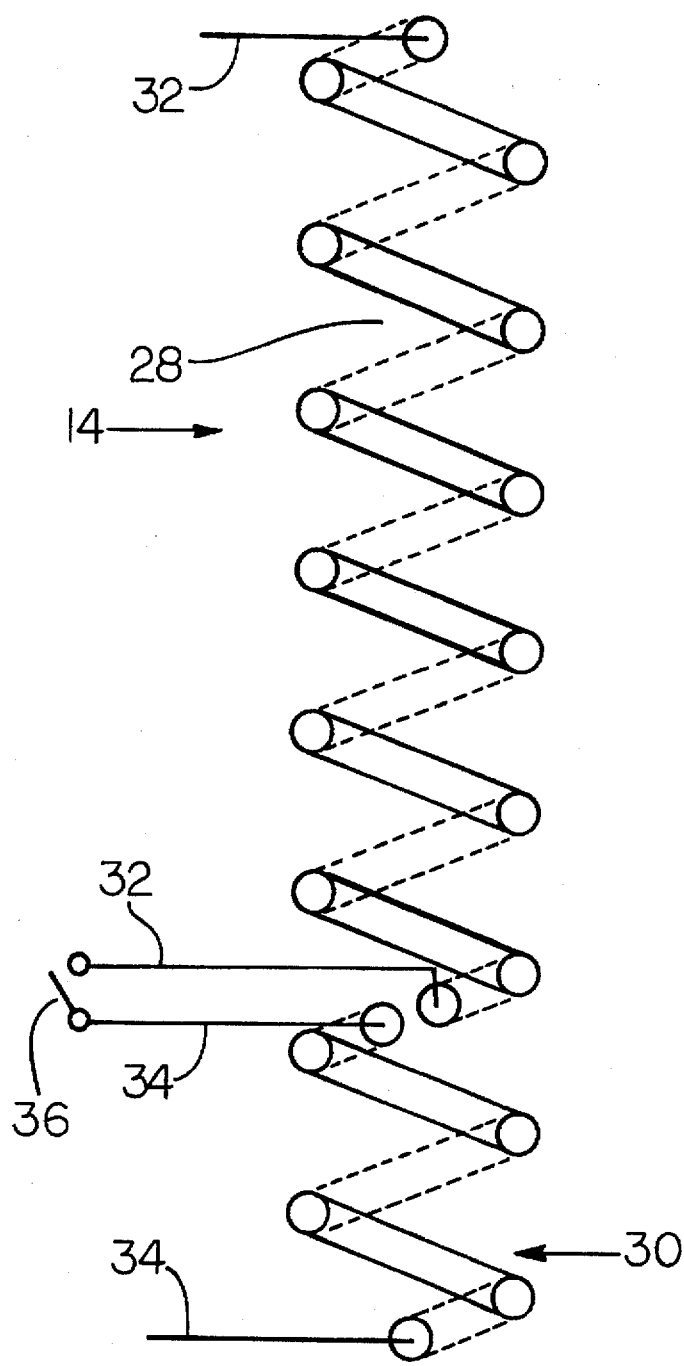
FIG. 6 is a side view of the helical electrode portion without the catheter body showing the helical electrode portion in two sections.

The helical electrode portion (16) preferably is divided into two or more separate sections (28, 30). See FIG. 6. Each section of the helical electrode portion is connected to a separate electrode conductor (32, 34) passing through a lumen of the catheter body. The individual sections of the helical electrode portion can then operate separately or, by use of a conventional switch mechanism (36), can operate in unison. By this mechanism separate sections of the helical electrode portion can map or sense different sections of the heart tissue without relocation of the helical electrode portion. By connecting the separate sections of the helical electrode portion together, a single ablation catheter can be formed. By opening and closing the switch (36) between the separate sections of the helical electrode portion, longer or shorter ablation catheters can be produced to ablate longer or shorter tracks of cardial tissue.

Figure 7:
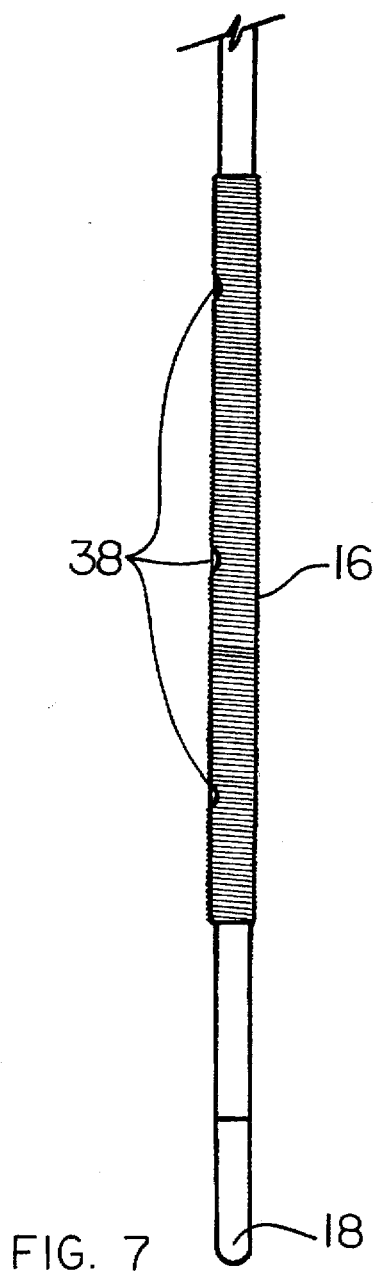
FIG. 7 is a side view of the distal end portion of the ablation catheter showing the helical electrode portion with thermocouple devices.

To monitor the amount of energy utilized for the ablation burn during the procedure, thermosensing detectors (38) preferably are secured to the helical electrode portion. See FIG. 7. For example, thermistors or preferably thermocouples, which sense the temperature at the surface of the coiled electrode, are secured, preferably at the beginning, middle and end of the helical electrode portion. When a plurality of sections of the helical electrode portion are utilized, separate thermosensing devices are preferably connected to each section to sense the temperature of the tissue at that section of the helical electrode portion during the ablation procedure. Each of these temperature sensing devices are designed to sense the temperature of the tissue adjacent to the surface of the helical electrode portion to assist in the determination of whether sufficient tissue contact has occurred to produce an effective ablation track.

In operation, a modified Seldinger technique is normally used for the insertion of the associated dilators, introducers and ablation catheters into the body. The appropriate vessel is accessed by needle puncture. The soft flexible tip of an appropriate sized guidewire is then inserted through, and a short distance beyond, the needle into the vessel. Firmly holding the guidewire in place, the needle is removed. The guidewire is then advanced through the vessel into the appropriate portion of the heart for the ablation procedure. Preferably, a preformed, shaped guiding introducer or guiding introducer system such as those disclosed in copending application Ser. No. 08/272,014, now U.S. Pat. No. 5,575,766 are utilized to assist in proper placement of an ablation catheter in the heart. See FIG. 8. With the guidewire in place, the dilator is then placed over the guidewire with the appropriate guiding introducer, or guiding introducer system, to be used placed over the dilator. The dilator and the guiding introducer or guiding introducer system generally form an assembly to be advanced together along the guidewire into appropriate vessel. After insertion of the assembly, the guidewire is then withdrawn.

The guiding introducer or guiding introducer system for use in the heart is then passed over the guidewire through its lumen and positioned to allow ablation and mapping procedures to be performed at the appropriate location in the heart. Once the guiding introducer or guiding introducer system is in place at the appropriate location within the heart, the ablation catheter (10) is advanced through the lumen of the guiding introducer or guiding introducer system. The distal end of the ablation catheter, including the helical electrode portion (16) of the ablation catheter, is then extended through the distal portion of the guiding introducer or guiding introducer system. After the desired location for ablation is determined, the uncoated portion (24) of the helical electrode portion (16) of the ablation catheter (10) is placed securely and firmly against the cardiac tissue. Ablation of the adjacent cardiac tissue then occurs. Thermosensing devices (38) associated with the helical electrode portion (16) assist in determining whether sufficient energy has been applied to the tissue to create an adequate linear scar. In addition, the helical electrode portion can be divided into separate sections (28, 30) to ablate shorter or longer tracks in the heart. After the ablation procedure is completed, the uncoated portion (24) of the helical electrode portion may be utilized as a sensing system to determine if the arrhythmia has been eliminated at the particular location within the heart. Additional ablation tracks can then be produced using the guiding introducers or a guiding introducer system and the ablation catheter at the same or different locations within the heart.

Pharmacological treatments may also be used in combination with ablation procedures to relieve the atrial arrhythmia.

It will be apparent from the foregoing that while particular forms of the invention have been illustrated and described, various modifications can be made without departing from the spirit and scope of the invention. Accordingly, it is not intended that this invention be limited except as by the appended claims.

I claim:

1. A catheter for mapping or ablating human tissue comprising a catheter body with proximal and distal ends and an outside surface, containing an electrode comprising an electrode conductor secured to a helical electrode portion with proximal and distal ends, wherein said helical electrode portion contains individual turns with an outside surface, wherein the individual turns are separated by a consistent, linear space, wherein the helical electrode portion is secured to the outside surface of the catheter body and wherein the turns of the helical electrode portions are secured to the catheter body by securing them within grooves in the catheter body of at least about 40 percent of the cross-section of an individual turn.

2. The catheter of claim 1 wherein the distance between individual grooves is approximately equal.

3. A process for the ablating of human tissue comprising (a) introducing into the human body a guiding introducer of guiding introducer system containing at least one lumen running therethrough, (b) directing the guiding introducer of guiding introducer system to human tissue within the human body to be ablated, (c) introducing into the lumen of the guiding introducer an ablation catheter comprising a catheter body with proximal and distal ends and an outside surface, containing one or more lumen running therethrough, and an electrode, wherein said electrode comprises one or more electrode conductors passing through one or more of the lumen of the catheter secured to a helical electrode portion containing individual turns each with an outside surface, wherein individual turns are separated by a consistent, linear space, wherein said helical electrode portion is secured to the outside surface of the catheter body, and wherein the turns of the helical electrode portions are secured to the catheter body by securing them within grooves in the catheter body of at least about 40 percent of the cross-section of an individual turn, (d) ablating the human tissue by use of the ablation catheter.

4. The process of claim 3 wherein the distance between the grooves is approximately the same.

* * * * *